US011047772B2

(12) United States Patent
Mäkelä

(10) Patent No.: US 11,047,772 B2
(45) Date of Patent: Jun. 29, 2021

(54) SYSTEM AND METHOD FOR DETERMINING AN AMOUNT OF FUNGAL PARTICLES IN AIR

(71) Applicant: Oy Fiseca Ltd., Helsinki (FI)

(72) Inventor: Hannu Mäkelä, Hameenlinna (FI)

(73) Assignee: Oy Fiseca Ltd., Helsinki (FI)

( * ) Notice: Subject to any disclaimer, the term of this patent is extended or adjusted under 35 U.S.C. 154(b) by 227 days.

(21) Appl. No.: 16/468,088

(22) PCT Filed: Nov. 12, 2017

(86) PCT No.: PCT/EP2017/082483
§ 371 (c)(1),
(2) Date: Jun. 10, 2019

(87) PCT Pub. No.: WO2018/108946
PCT Pub. Date: Jun. 21, 2018

(65) Prior Publication Data
US 2019/0331557 A1    Oct. 31, 2019

(30) Foreign Application Priority Data
Dec. 12, 2016    (EP) ..................................... 16203354

(51) Int. Cl.
*G01N 1/22*    (2006.01)
*B01L 5/02*    (2006.01)
(Continued)

(52) U.S. Cl.
CPC .............. *G01N 1/2205* (2013.01); *B01L 5/02* (2013.01); *G01N 1/4044* (2013.01);
(Continued)

(58) Field of Classification Search
CPC ..... B01L 2200/0631; B01L 2200/0652; B01L 2200/10; B01L 2300/0636;
(Continued)

(56) References Cited

U.S. PATENT DOCUMENTS

| 2004/0038385 A1 | 2/2004 | Langlois et al. |
| 2006/0257853 A1 | 11/2006 | Herman |

(Continued)

OTHER PUBLICATIONS

International Search Report and Written Opinion, Application No. PCT/EP2017/082483, dated Sep. 26, 2018.

*Primary Examiner* — Jennifer Wecker
(74) *Attorney, Agent, or Firm* — Ziegler IP Law Group, LLC (57) ABSTRACT

A system for determining an amount of fungal particles in air in a building includes including: an air inlet connected to a filter for filtering particles having a size of 1-120 μm; means for collecting fungal particles from the filtered particles and transferring the collected fungal particles to at least one sample cuvette; means for dry denaturation of the fungal particles; means for producing a voltage change of the dry denaturised fungal particles and means for detection of voltage changes caused by the dry denaturised fungal particles to obtain voltage change data; means for collecting a sample; means for wet denaturation of the fungal particles subsequent to the detection of voltage changes. The system further includes at least two of means for immunological detection of the fungal species in the sample to obtain immunological data; means for measuring glucose concentration of the sample to obtain glucose concentration data; means for measuring light emission of the sample to obtain light emission data.

12 Claims, 5 Drawing Sheets

(51) Int. Cl.
*G01N 1/40* (2006.01)
*G01N 1/44* (2006.01)
*G01N 21/31* (2006.01)
*G01N 27/74* (2006.01)
*G01N 33/569* (2006.01)
*G01N 21/21* (2006.01)
*G01N 21/77* (2006.01)

(52) U.S. Cl.
CPC .............. *G01N 1/4077* (2013.01); *G01N 1/44* (2013.01); *G01N 21/21* (2013.01); *G01N 21/31* (2013.01); *G01N 21/77* (2013.01); *G01N 27/74* (2013.01); *G01N 33/56961* (2013.01); *B01L 2200/0631* (2013.01); *B01L 2200/0652* (2013.01); *B01L 2200/10* (2013.01); *B01L 2300/0636* (2013.01); *B01L 2300/0681* (2013.01); *G01N 2001/4088* (2013.01); *G01N 2333/37* (2013.01)

(58) Field of Classification Search
CPC . B01L 2300/0681; B01L 5/02; G01N 1/2202; G01N 1/2205; G01N 1/4044; G01N 1/4077; G01N 1/44; G01N 15/0656; G01N 2001/2223; G01N 2001/4088; G01N 2015/0046; G01N 2015/0088; G01N 21/21; G01N 21/31; G01N 21/77; G01N 2333/37; G01N 27/74; G01N 33/56961

See application file for complete search history.

(56) References Cited

U.S. PATENT DOCUMENTS

| | | | |
|---|---|---|---|
| 2011/0256630 A1 | 10/2011 | Clinton | |
| 2012/0105839 A1* | 5/2012 | Novosselov | G01N 1/2208 356/301 |
| 2012/0174650 A1* | 7/2012 | Ariessohn | B08B 7/026 73/23.2 |

* cited by examiner

SYSTEM AND METHOD FOR DETERMINING AN AMOUNT OF FUNGAL PARTICLES IN AIR

TECHNICAL FIELD

The present disclosure relates generally to monitoring the quality of air, and more specifically, to a system and a method for determining an amount of fungal particles in air in a building.

BACKGROUND

Indoor air quality (IAQ) has become an important consideration in creating satisfactory indoor environments, particularly in homes, office buildings, schools and health care facilities. When structural parts of buildings that are used for commercial or residential purposes get wet or humid, indoor air contaminants such as rot or decay fungus, mildews, yeasts and bacteria start to proliferate. These factors that influence the quality of indoor air are the most difficult to monitor. These organisms can diffuse to persons through the air, in various stages of their lives such as spores, different volatile compounds and/or as airborne cell wall particles caused e.g. by decay. Some of the volatile compounds can form a direct health risk and their influence may in some instances be permanent, even if the person moves to a clean environment. The spores may have a direct influence to the functioning of lungs and the blood circulation of lungs and cause serious lungs-related health hazards to persons who inhale them.

Before the air quality in these environments can be improved, the air quality has to first be measured and analysed to determine if a problem exists and to diagnose the nature of the problem. Typical systems and methods for analysing the quality of air are very expensive. They may also be insufficient to obtain a customized indoor air quality assessment of a building and further to provide a customized set of recommendations for solving any potential air quality problems that may be uncovered. Momentary changes in the cleanliness of the air in the building might affect the interpretation of results, depending on when the sample is taken. Some methods that are specific to the species of the organisms present in the air require the sampled species to be alive in order to obtain a result. Therefore for example inert spores (e.g. cysts, Meiosporangia, Ascospores, Macrocysts, Sclerotia, Oospores, Zygospores, and Chlamydospores including Hülle cells) or dead spores are not visible in the laboratory measurements following the sampling (e.g. with an Andersen-collector) thus making them inconvenient for sampling and also inaccurate. Furthermore, to our best knowledge, none of the existing methods provide equal growing conditions for every species in petri dishes. Indeed, there are substantial differences between species on how they grow on a given substrate. Highly skilled experts may be required in some or all of the stages of the analysis to obtain a reliable measurement result. The typical system and the method also does not take into account movements of the air in the building that might have a significant effect in the measurement results. Further, the spores typically deposit on surfaces of the building during the night, and may rise into the air again when the room is in active use. Thus, the time of the day has a high impact on the measurement results.

Still further, in some cases only larger amounts of fungal particles cause problems to the users of the building. However, it would be beneficial to be able to monitor the quality of air in a continuous manner, in order to detect early changes and thus to be able to react before the problems are too serious. This would benefit both the society (less health costs) as well as the owners of the building (early reparations are typically cheaper).

Therefore, in light of the foregoing discussion, there exists a need to overcome the aforementioned drawbacks in existing systems and methods for determining a reliable customized indoor air quality assessment result of a building over a period of time without requiring highly skilled experts for performing laboratory experiments of air samples.

SUMMARY

The present disclosure provides a system for determining an amount of fungal particles in air in a building, comprising
an air inlet connected to a filter for filtering particles having a size of 1-120 µm,
means for collecting fungal particles from the filtered particles and transferring the collected fungal particles to at least one sample cuvette,
means for dry denaturation of the fungal particles,
means for producing a voltage change of the dry denaturised fungal particles and means for detection of voltage changes caused by the dry denaturised fungal particles to obtain voltage change data,
means for collecting a sample of the dry denaturised fungal particles,
means for wet denaturation of the sample, wherein the system further comprises at least two of
means for immunological detection of the fungal species in the sample to obtain immunological data,
means for measuring glucose concentration of the sample to obtain glucose concentration data,
means for measuring light emission of the sample to obtain light emission data,
and the system comprises means for collecting and transmitting the obtained data to a processor, the processor comprising a database of reference data and being configured to compare the reference data to the obtained data for determining the amount of fungal particles in air in the building.

The present disclosure also provides a method for determining an amount of fungal particles in air in a building, comprising:
periodically injecting a sample of air to a filter for filtering particles having a size of 1-120 µm,
collecting fungal particles from the filtered particles,
transferring the collected fungal particles to a sample chamber,
dry denaturising the fungal particles,
detecting voltage changes caused by the denatured fungal particles,
collecting a sample of the denatured fungal particles,
wet denaturising the sample,
analysing the sample in parallel by at least two analysis methods, wherein the analysis methods are selected from immunological detection, glucose measurement and light emission measurement, to obtain measurement data, and
comparing reference data to obtained measurement data.

Embodiments of the present disclosure substantially eliminate or at least partially address the aforementioned problems in the prior art, and thus the present disclosure provides a method and a system that autonomously determines microbial quality of air in a building at predefined intervals without requiring any highly skilled experts for performing laboratory experiments of sample liquids. This leads to an early detection of any problems in the building structure, as also small increases in the amount of fungal particles can be detected. The present system and method may be carried out automatically.

Additional aspects, advantages, features and objects of the present disclosure are made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

The present disclosure provides a system for determining an amount of fungal particles in air in a building, comprising
    an air inlet connected to a filter for filtering particles having a size of 1-120 μm,
    means for collecting fungal particles from the filtered particles and transferring the collected fungal particles to at least one sample cuvette,
    means for dry denaturation of the fungal particles,
    means for producing a voltage change of the dry denaturised fungal particles and means for detection of voltage changes caused by the dry denaturised fungal particles to obtain voltage change data,
    means for collecting a sample of the dry denaturised fungal particles, means for wet denaturation of the sample, wherein the system further comprises at least two of means for immunological detection of the fungal species in the sample to obtain immunological data, means for measuring glucose concentration of the sample to obtain glucose concentration data, means for measuring light emission of the sample to obtain light emission data, and the system comprises means for collecting and transmitting the obtained data to a processor, the processor comprising a database of reference data and being configured to compare the reference data to the obtained data for determining the amount of fungal particles in air in the building.

In the present system and method, there are thus the following steps: collection of particles, dry denaturation (various possible means are given below), voltage change measurement, sample collection, wet denaturation and further analysis. In an optional embodiment, the sample is again submitted to alternative voltage change measurement from the wet denaturised sample. The various means and steps are thus typically carried out in the given order, and each step is typically carried out on the results of the preceding step (treated sample or particles).

In an embodiment, the system comprises the means for detection of voltage changes and the means for immunological detection. In another embodiment, the system comprises the means for detection of voltage changes and the means for measuring glucose concentration of the sample. In yet another embodiment, the system comprises the means for detection of voltage changes and the means for measuring light emission of the sample. In yet another embodiment, the system comprises the means for detection of voltage changes, the means for immunological detection and the means for measuring glucose concentration of the sample. In yet another embodiment, the system comprises the means for detection of voltage changes, the means for immunological detection and the means for measuring light emission of the sample. In yet another embodiment, the system comprises the means for detection of voltage changes, the means for immunological detection, the means for measuring glucose concentration of the sample and the means for measuring light emission of the sample.

In yet another embodiment, the system comprises the means for detection of voltage changes, the means for measuring glucose concentration of the sample and the means for measuring light emission of the sample. In yet another embodiment, the system comprises the means for immunological detection and the means for measuring glucose concentration of the sample. In yet another embodiment, the system comprises the means for immunological detection and the means for measuring light emission of the sample. In yet another embodiment, the system comprises the means for immunological detection, the means for measuring glucose concentration of the sample and the means for measuring light emission of the sample. In yet another embodiment, the system comprises the means for measuring glucose concentration of the sample and the means for measuring light emission of the sample. Such means for measuring light emission of the sample means a means capable to measure emission and/or absorbance caused by the interaction of light targeted into the sample.

In the present description, the term measurement means is used as a general term describing the various means capable of measuring a characteristic of the sample, such as the means for detection of voltage changes caused by the fungal particles, the means for immunological detection of the fungal species in the sample, the means for measuring glucose concentration of the sample, the means for measuring light emission of the sample, and the other possible measurement means listed below.

The nature and number of the above-listed means is selected, i.a., according to the desired measurement results and the size of the system. Likewise, the pre-determined intervals for measurement can be set either by the manufacturer of the system and/or by the user. For example, if the user knows that the premises where the system is set up will be left unused for a given time during cold season, the system may be set to measure only once a day or once a week. If the premises is left unused for a given time during a warm, humid season, the measurements may be set up more frequently.

The order of the various means may also vary. Typically, the air inlet, filter and means for collecting filtered particles are arranged consecutively in the system. However, thereafter, the various means may be arranged in any suitable manner. In one embodiment, means for increasing voltage of the fungal particles is arranged after the means for collecting the filtered particles, followed by voltage measurement means (either dry from the sample cuvette or from a wet sample), thereafter followed by denaturation and glucose measurement. This may still further be supplemented by the immunological measurement means and the luminance measurement means, in either order. The system may also comprise several parallel measurement routes, or the measurement methods may be carried out consecutively. Likewise, the system may be arranged to perform parallel measurements (i.e. the same measurement on two or more parallel samples) and to combine the obtained results using statistical analysis.

According to an embodiment, the means for increasing voltage of the fungal particles is a means that irritates the particles for example with UV-light, IR-light, ultrasound and/or friction (for example by colliding the particles with each other and/or chamber walls), with voltage ranging from 1 kV to 20 kV. According to another embodiment, the means for collecting the filtered particles can be for example an electrostatic filter. The voltage measurement means is based on changes in the electrical charge of the fungal particles, and it may be measured using widely known physical principles or methods (e.g. Faraday-electrolysis method, Millikans's oil-drop method, an interference method using Josephson's effect, Quantum Hall-effect or a committee on data (CODATA) method with "watt balance" to receive accurate Planck's constant etc.) with help of an appropriate sensor or a measurement unit. Schottky's shot-noise method may be used to enhance the accuracy of the measurement.

The system thus autonomously determines quality of air in a building at several intervals (e.g. predefined intervals) by determining the amount of fungal particles (e.g. mould spores) in the air without requiring highly skilled experts for performing laboratory experiments on sample liquids. This system is cost effective and faster when compared to other existing systems as the existing systems may require experts for performing laboratory experiments to determine the amount of fungal particles in the air, in which the experts may take several days or weeks for performing the laboratory experiments. Further, the system does not require manual intervention to take samples (e.g. sample liquids) to perform laboratory experiments as it is automated. The system further measures microbial quality of the air (e.g. amount of fungal particles in air) several times in a given time unit (e.g. 24 hours) to minimise variances of measurement results (e.g. concentration of glucose, light emission, voltage changes, immunological function of fungal particles in the sample liquids etc.). The system may collect the measurement results and data and store it in a desired form.

The system further increases a number of measurements per time unit to an optimum level. Furthermore, if desired, the system may be arranged in a ventilation system conduct to function as a unit to clean the air by removing fungal particles, especially in environments using a closed circuit for air. The system further continuously monitors changes in the microbial quality of the air. The system detects even small changes in the quality of the air and reacts to it before larger damage happens to the building. The system can be customized in various sizes based on a size of the building and the desired measurement accuracy. As the system may also be made portable, it can be installed with other technical equipment for continuously monitoring microbial air quality of the building (e.g. the amount of fungal particles present in air). The system may be installed with a ventilation system of the building, for example when the building is being built. The system may be installed in the building even at a later stage. In an embodiment, one or more systems are installed at various locations of the building when the building is large. The one or more systems may be communicatively connected to a processor which obtains all the measurement data and results (e.g. one or more of concentration of glucose, light emission, voltage changes, immunological function of fungal particles in the sample liquids etc.). The processor may analyse the obtained measurement data locally or remotely.

The air inlet obtains a sample of air present inside the building. A nozzle may be used instead of the air inlet to obtain air present inside the building. In an embodiment, the air inlet comprises a suction fan, a pump, a blower or any suitable means to suck the air. Minimum air volume of the air inlet may range from 80 litres to 150 litres (l). In various embodiments, the minimum air volume of the air inlet may be from 80, 85, 90, 95, 98, 100, 115, 120, 130 or 140 litres up to 85, 90, 95, 98, 100, 115, 120, 130, 140, 145 or 150 litres. A preferable air volume of the air inlet may range from 500 l to 10000 l. In certain embodiments, the preferable air volume of the air inlet may be from 500, 550, 600, 700, 900, 1000, 1200, 1500, 2000, 2500, 3000, 3500, 4000, 4500, 5000, 5500, 6000, 6500, 7000, 7500, 8000, 8500 or 9000 litres up to 550, 600, 700, 900, 1000, 1200, 1500, 2000, 2500, 3000, 3500, 4000, 4500, 5000, 5500, 6000, 6500, 7000, 7500, 8000, 8500, 9000, 9500 or 10000 litres.

A preferable air flow of the air inlet may range from 10 litre per minute to 500 litre per minute (l/min). In certain embodiments, the preferable flow rate of the air inlet may be from 10, 15, 20, 25, 35, 50, 75, 100, 125, 175, 200, 250, 300, 350, 375 or 400 l/min up to 15, 20, 25, 35, 50, 75, 100, 125, 175, 200, 250, 300, 350, 375, 400, 450, 500 l/min.

The air inlet may be made up for example of plastic, glass, iron, wood or a galvanized metal. The air inlet is connected to a filter for filtering particles having a size ranges from 1 μm to 120 μm (1 micrometre to 120 micrometres). In various embodiments, the size of particles that are filtered may be for example 1, 2, 3, 4, 5, 10, 15, 20, 25, 30, 35, 40, 45, 50, 55, 60, 65, 70, 75, 80, 85, 90, 95, 100, 105, 110 or 115 µm up to 2, 3, 4, 5, 10, 15, 20, 25, 30, 35, 40, 45, 50, 55, 60, 65, 70, 75, 80, 85, 90, 95, 100, 105, 110, 115 or 120 µm. The filtered particles may be bacteria, fungi, protozoa, algae, spores, pollen, lichen, archaea, viruses etc. In an embodiment, the filter may comprise at least one sub-filter and optionally at least one additional filter to filter the particles from air.

The fungal particles are then collected from the filtered particles using a means for collecting fungal particles, such as an electrostatic filter or a microperforated atomising filter. The means for collecting fungal particles transfer the fungal particles to at least one sample cuvette, if a sample cuvette is required. The transfer can be carried out using for example a microperforated atomising filter, an air blower, air suction, or by dissolving the sample into a liquid and injecting the desired amount of solution into the next phase or phases, for example with an autosampler similar to what is used in HPLC-, GC-MS- and GC-FID-devices. The at least one sample cuvette may be an optical glass cuvette, a plastic cuvette, a fused quartz cuvette, an ultraviolet (UV) quartz cuvette, an infrared (IR) quartz cuvette etc. In an embodiment, the at least one sample cuvette may be a reusable quartz cuvette, and the reusable quartz cuvette may be washed and dried after each sampling during measurement process. In another embodiment, the sample cuvette is a single-use cuvette with a cassette for each sampling. In yet another embodiment, the at least one sample cuvette may be a new cuvette to carry the fungal particles for each sampling during measurement process. The means for collecting fungal particles may also transfer the fungal particles to more than one sample cuvette, i.e. it may divide the fungal particles into two, three, four, five or more sample cuvettes. These sample cuvettes may be arranged in a single sample chamber or in two, three, four or more different sample chambers.

The present system, in case it uses more than one sample cuvette and/or measurement means that are not directly applicable to the sample cuvette, comprises the required means for transferring and moving the various sample cuvettes and/or measurement means. These means can be any kind of means known as such in the field of automation, for example automated arms or autosampler similar to what is used in HPLC-, GC-MS- and GC-FID-devices. In such a case, the processor is configured to control and activate these means. Indeed, the present system is typically configured for detecting a certain type or types of fungal particles, i.e. built and programmed for certain use.

The at least one sample cuvette may be heated to denaturize the fungal particles (e.g. denaturation of a mould spore proteoglycan). Denaturisation may be carried out for example at a temperature of 40-85° C. for a period of time from 10 s to 10 minutes, thus breaking the chemical and physical bonds between molecules and atoms or elements. Denaturation may also be carried out using IR- or UV-light, by using lytic enzymes or a high-voltage treatment. By denaturation in this description it is meant breaking down the biomolecules into smaller molecules, thus enhancing the electrochemical charge and simultaneously revealing the chemical structures typical to fungal species. By dry denaturation it is meant any method (such as use of heat, IR- or UV-light) that does not include adding a liquid to the material to be denatured. By wet denaturation it is meant any method (such as using lytic enzymes) which includes adding a liquid to the material to be denatured. The at least one sample cuvette may also control a concentration of the sample liquid that comprises the fungal particles to increase a spore concentration for the measurement process to follow. The heating also has the advantage of creating an optimal measuring environment from biochemical and biophysical perspective for an automated system instead of laboratory-dependent detection.

The obtained data (e.g. measurement data) may comprise results related to a temperature of the air, a relative air water content, an absolute air water content, an output measurement of the air through an air flow meter, a glucose concentration of the sample liquid, immunological functions of the fungal species in the sample liquid, a light emission of the sample liquid and voltage changes of the sample liquid. The processor is thus preferably configured to use all the obtained data in the comparison with the reference data. Reference data stands for data previously collected using existing methods. The reference data is variable during the following steps of the process where the statistical analyses are being carried out.

The reference data may be measured from a unit of air volume and the microbiological organisms contained therein. Using existing and valid measurement methods, a statistically sufficient amount of reference data may be obtained from the unit of air volume and microbiological organisms contained therein, in a manner that is scientifically considered sufficient and suitable. The measurements of the reference data may be carried out in supervised laboratories, even though many contaminated buildings may be used as sites for measuring the reference data. Further, it is nearly impossible to standardize the conditions in such buildings and remove the effect of outside factors. Laboratory conditions refer to, for example clean rooms specifically designed for growing microbes, where the conditions are in a normal temperature and pressure (NTP) state. In an embodiment, the reference data comprises predefined measurements (e.g. predefined measurements of glucose concentration, predefined measurement of the light emission etc.).

The processor may obtain the obtained data (e.g. measurement data) from each measurement process and divide the obtained data to parametric and non-parametric variables. The processor may calculate correlations and a linear regression factor between the variables to compare the variables to the reference data in a controlled environment to obtain a final data. The final data may be used to provide a simple graphical output that represents a variation and a direction of the concentration of the fungal particles in a unit of sample liquid (e.g. fungal particles*$m^3$). The final data may be displayed in a user interface in a simplified form (e.g. using terms like clean, endangered, polluted) or in absolute values for scientific purposes, depending on the concentration of the fungal particles. In an embodiment, numerical values of the obtained data may be transformed to simple graphical representations that represent the quality of the air. Using a change in the measurement data obtained from different measurement units of the system, a source of a microbial damage may be located more accurately without invasion of a structure of the building. The system may also be configured to communicate the measurement data to a central monitoring arrangement, for example in the case of an apartment building or a group of apartment buildings. The system may still further be configured to send a warning to a user's mobile device, in case actions are required.

In an embodiment, the system comprises several measurement units and processors to obtain measurement data. The system may also comprise several measurement units and one processor that combines the measurement data from different measurement units (comprising an air inlet, filter, collecting means for fungal particles, heating means and the detection and/or measurement means listed above).

Further, a calculation algorithm may be used to process the final data into a readable form at the processor. The calculation algorithm may be, in statistical terms, a log-linear regressive function and may vary based on requirements. Variance in the calculation algorithm may comprise environmental factors. The environmental factors may comprise baseline values of the parameters to be measured and factors that have a predictable effect on the measurement results/data (e.g. a temperature, a relative humidity of the air, a time of day, a time of the year that describe turbulences of the air and microbiological organisms from nature).

In an embodiment, the measurement data may be transferred to a central unit to determine a final data. The central unit may be communicatively connected to the system. The final data may be transferred to a user interface of a reading device using a wireless network, a local area network or a wide area network etc. The reading device may be communicatively connected to the system. The reading device may be a portable communication device (a cell phone, a computer, a tablet etc. or it may be a user interface arranged on the system itself).

According to an embodiment, the means for denaturisation of the fungal particles may be for example means for heating the at least one sample cuvette for denaturation of the fungal particles and for concentration of a sample liquid, or it may be a collector-voltage measurement chamber. Furthermore, these means may for example include e.g. lytic enzymes mentioned above, chemical treatment with e.g. formaldehyde, ethanol or methanol and physical treatment such as ultrasound, elevated temperature etc.

According to an embodiment, the means for collecting fungal particles is selected from a filter, a condensation plate and a bubbler liquid filter, in addition to those listed above. A bubbler liquid filter is commercialised for example by Righton Instruments Company (L100 Bubble Tube Liquid Level System) The filter may be for example an electrostatic filter, which may electrostatically charge the fungal particles to attract the fungal particles, after pre-filtering the non-desirable particles, and the transfer of the fungal particles is typically carried out as explained above. The condensation plate may condense the charged or non-charged fungal particles. In an embodiment, the fungal particles are obtained using a bubbler liquid filter with a micro-perforated diaphragm or any suitable means, including e.g. HEPA-filters, electrostatic filters, disposable and/or changeable porous filters etc. The fungal particles may be collected using the means for collecting fungal particles in at least one sample cuvette and a chamber armed with a voltage regulator and a non-conducting wall material. Changes in the electrical charge of the fungal particles may be measured using known physical principles and methods, as explained above. For example, it is possible to use Faraday-electrolysis method (using an ammeter device measuring the amount of substance formed at each electrode, thus quantifying the charge flow through the device cell), Millikans's oil-drop method (using a capacitor with two metal plates or surfaces with electrically charged oil droplets between them), an interference method using Josephson's effect (i.e. application of Josephon's junction or SQUID, i.e. superconducting quantum interference device for detecting extremely low currencies), Quantum Hall-effect or a committee on data (CODATA) method with "watt balance" to receive accurate Planck's constant (although this method is less likely to be used, due to its temperature demands; it qualifies the Hall conductance transition in low temperatures and in the presence of a magnetic field to a detectable quantum Hall transition) etc., with help of an appropriate sensor or a measurement unit. Schottky's shot-noise method (also known as Poisson noise to detect the interference caused in devices measuring electrical charge) may be used to enhance the accuracy of the measurement. In an embodiment, the system comprises a filter heat control that controls the heat of the various temperature dependent phases.

According to another embodiment, the means for immunological detection is a group of at least two species specific antigen based immunological test strips. A small droplet of liquid sample can be transferred on the test strip by an automatic sampler for example. Such test strips are commercially available and know to a person skilled in the art. The at least two species specific antigen based immunological test strips may be used for detecting the most harmful fungal particles (e.g. *Aspergillus, Trichoderma, Penicillium, Stachybotrys* etc.). The immunological detection of the at least two species may be based on an antigenic reaction between an antibody and the antigen (e.g. a structural compound or compounds found in the fungal particle), e.g. chitin and beta(1→3)(1→6)-glucan producing fungal, but not species specific reaction, using fungal, e.g. rot enzyme-specific detection and/or basic structural molecules. Such detection may be based on e.g. manganese peroxidase and laccase or specifically against certain species of up-raised antibodies. Enzymes mentioned here are be part of the decomposition phase of complex molecules and release a part of the glucose molecules for glucose measurement. Free glucose is needed for this measurement only, while others process use material from a collector and/or charger chamber (for example the sample cuvette).

According to yet another embodiment, the means for measuring glucose concentration comprises means for treating the sample using temperature and reduced potential of hydrogen (pH) and the means is selected from means based on chemical indication, optical polarisation, blue light absorption or magnetic mutual inductance. A small amount of the sample liquid may be transferred to at least one sample cuvette using a pipette, a pumping means or a suction means for measuring glucose concentration. The sample liquid may be pre-treated with lytic enzymes. The lytic enzymes comprise at least one of a chitinase, a glucanase, a proteinase or a peroxidase. In an embodiment, the sample liquid is transferred to the at least one sample cuvette with a preferable temperature ranges from 40° C. to 85° C. and a preferable potential of hydrogen (pH) ranges from 0 to 3. In certain embodiments, the preferable temperature while transferring the sample liquid to the at least one sample cuvette may be from 40, 45, 50, 55, 60, 65, 70 or 80° C. up to 45, 50, 55, 60, 65, 70, 80 or 85° C. In certain embodiments, the preferable pH while transferring the sample liquid to the at least one sample cuvette may be about 1, 2 or 3, or it may be from 0, 0.2, 0.5, 0.7, 1, 1.3, 1.5, 1.8, 2, 2.2, 2.5 or 2.7 up to 0.2, 0.5, 0.7, 1, 1.3, 1.5, 1.8, 2, 2.2, 2.5, 2.7 or 3. A decomposition time of the fungal particles may range from 20 seconds to 20 minutes. In an embodiment, the system measures the glucose measurements using glucose concentration measurement devices. The glucose concentration measurement devices may be for example a One Touch Ultra Mini® blood glucose monitoring system, a Free Style Lite® blood glucose monitoring system and/or magnetic mutual inductance etc. In another embodiment, the system comprises a level sensor that measures a level of sample liquid in the at least one sample cuvette. According to yet another embodiment, the means for measuring light emission comprises means for treating the sample using increased potential of hydrogen (pH), solvent and at least one light emission aiding component (such as a fluorophore when fluorescence is measured), excitation means and optical emission measurement means. The sample liquid (e.g. ranges from 0.1 microlitre to 2 millilitre) may be obtained in at least one sample cuvette using a pipette or suction means and pre-treated for measuring light emission. In certain embodiments, a quantity of the obtained sample liquid in at least one sample cuvette may be from 0.1, 0.5, 1, 1.5, 2, 5, 10, 20, 30, 50, 75, 100, 150, 200, 300, 400, 500, 900, 1000, 1200, 1500 or 1700 microlitres up to 0.5, 1, 1.5, 2, 5, 10, 20, 30, 50, 75, 100, 150, 200, 300, 400, 500, 900, 1000, 1200, 1500, 1700, 1900 or 200 microlitres.

In a further embodiment, the system comprises means for controlling the physio-chemical conditions of the system. Such controlling means may be used to maintain the conditions such that they are ideal for the execution of the various measurements. These conditions may require e.g. certain temperature, pH etc.

In an embodiment, the sample liquid is transferred to the at least one sample cuvette with a preferable temperature ranges from 20° C. to 60° C. and a preferable potential of hydrogen (pH) ranges from 9 to 11. In certain embodiments, the preferable temperature while transferring the sample liquid to the at least one sample cuvette may be from 20, 25, 30, 35, 40, 45, 50 or 55° C. up to 25, 30, 35, 40, 45, 50, 55 or 60° C. etc. In certain embodiments, the preferable pH while transferring the sample liquid to the at least one sample cuvette may be from 9, 9.2, 9.5, 9.7, 10, 10.2, 10.5 or 10.8 up to 9.2, 9.5, 9.7, 10, 10.2, 10.5, 10.8 or 11. Then, formaldehyde in ranges from 3% to 6% concentration in distilled water may be added to the at least one sample cuvette comprising the sample liquid. In certain embodiments, the concentration of the formaldehyde in distilled water may be about 4%, 5% or 6%. The fluorophores in ranges from 0.1% to 5% concentration may be then added to the sample liquid. In certain embodiments, the concentration of the fluorophores added in the sample liquid may be 0.4%, 0.8%, 1.2%, 2.6% or 5.5%. The fluorophores may be calcofluor, solophenyl Flavine 7GFE 500, or pontamine Fast Scarlet 4B etc. In an embodiment, the sample liquid may be treated for between 20 seconds to 20 minutes to measure fluorescence emission. The fluorescence emission may be measured using a luminance detector by exposing the pre-treated sample liquid to ultraviolet A (UVA) light, which is generated by an emitter. In an embodiment, when the pre-treated sample liquid comprising calcofluor is exposed to UVA, an excitation wavelength for the calcofluor may range from 300 nanometres to 400 nanometres with an optimum in 365 nanometres (nm), dichroic mirror or a filter may range from 350 nanometres to 450 nanometres with optimum in 400 nanometres and the fluorescence emission is at ranges from 400 nanometres to 500 nanometres with the optimum in 440 nanometres. In certain embodiments, the excitation wavelength for the calcofluor may be 320 nanometres, 370 nanometres, 380 nanometres or 395 nanometres etc. In certain embodiments, the dichroic mirror or the filter for the calcofluor may be 360, 375, 398, 420, 440 or 447 etc. In certain embodiments, the fluorescence emission for the calcofluor may be 430, 450, 475 or 495 etc. In another embodiment, when the pre-treated sample liquid comprising Solophenyl is exposed to UVA, an excitation wavelength for the Solophenyl may range from 440 nanometres to 520 nanometres with the optimum in 480 nanometres, the dichroic mirror or the filter may range from 480 nanometres to 520 nanometres with optimum in 505 nanometres and the fluorescence emission is at ranges from 480 nanometres to 570 nanometres with the optimum in 430 nanometres. In certain embodiments, the excitation wavelength for the Solophenyl may be 450 nanometres, 490 nanometres, 499 nanometres or 515 nanometres etc. In certain embodiments, the dichroic mirror or the filter for the Solophenyl may be 490, 500, 512 or 516 etc. In certain embodiments, the fluorescence emission for the Solophenyl may be 485, 505, 560 or 565 etc. In yet another embodiment, when the pre-treated sample liquid comprising Pontamine is exposed to UVA, an excitation wavelength for the Pontamine may range from 500 nanometres to 580 nanometres with the optimum in 480 nanometres, the dichroic mirror or the filter may range from 550 nanometres to 590 with optimum in 570 nanometres and the fluorescence emission is at ranges from 550 nanometres to 610 nanometres with the optimum in 590 nanometres. In certain embodiments, the excitation wavelength for the Pontamine may be 510 nanometres, 526 nanometres, 560 nanometres or 575 nanometres etc. In certain embodiments, the dichroic mirror or the filter for the Pontamine may be 565, 580, 583 or 585 etc. In certain embodiments, the fluorescence emission for the Pontamine may be 563, 576, 580 or 600 etc. The fluorescence emission may be measured using optical methods known in the art. In an embodiment, various light amplifiers (e.g. lamps, mirrors, lenses, light tubes etc.) are used to enhance the luminance before fluorescence/luminance detection.

The same considerations as above apply when another type of light emission is measured than fluorescence, as is readily known to a person skilled in the art of light emission measurement.

According to yet another embodiment, the system further comprises means for measuring flow of air at an air outlet of the means for collecting fungal particles. The air from which the fungal particles are separated are conducted through a pipe to an air flow meter. An air filter may precede the air flow meter. The flow of air may be measured using a hot wire anemometer or any other suitable means known in the art (e.g. an air balancing hood measurement, an airflow traverse in an exhaust duct or a plot fan airflow). A volume of the air may be used as a co-variable for determining the amount of fungal particles in air. In an embodiment, the system comprises a calibrated fan, a blower or a centrifugal pump to suck out the air from the system. According to yet another embodiment, the system further comprises at least one of a thermometer for obtaining temperature data, a means for measuring relative air water content for obtaining relative air water content data and a means for measuring absolute air water content for obtaining absolute air water content. These measurements would then also be communicated to the processor and taken into account in the calculation of final results.

According to yet another embodiment, the system further comprises a user interface for displaying the determined amount of fungal particles. The user interface preferably displays the determined amount of fungal particles in readable form. The determined amount of fungal particles may be displayed in a user interface of a laptop, a cellular phone, a tablet, a personal computer or a smartphone etc.

According to yet another embodiment, the system further comprises means for raising an alert when the amount of fungal particles in air deviates from target amount of fungal particles in air by a pre-defined amount. The means for raising the alert may be a sound alert, a short message sent (SMS) alert, a mail alert or a call alert etc. The pre-defined amount can be set either by the manufacturer of the system or by the user. The pre-defined amount may depend for example on the specific fungal particle or on the use of the building where the system is installed. For example, the pre-defined amount can be set lower in a school than in an office building.

According to yet another embodiment, the means for detection of voltage changes caused by the fungal particles is based on at least one of electrochemical detection and electrophysical detection. In an embodiment, the fungal particles are charged using the electrostatic filter and the changes in voltage in the filter are used to measure a count of the fungal particles. In an embodiment, a voltage applied for charging the fungal particles may range from 1 kV to 20 kV. In certain embodiments, the voltage applied for charging the fungal particles may be from 1, 2, 3, 5, 8, 10, 12, 15 or 18 kV up to 2, 3, 5, 8, 10, 12, 15, 18 or 20 kV. In an embodiment, free valence electrons are produced using ultra-violet, infra-red, ultrasound or friction to charge the fungal particles. In an embodiment, three measurements of the fungal particles may be used for analysing a quantity of the fungal particles, for example different methods for measuring a difference in voltage can be used.

The present disclosure provides a method for determining an amount of fungal particles in air in a building, comprising the steps of:
  periodically injecting a sample of air to a filter for filtering particles having a size of 1-120 μm,
  collecting fungal particles from the filtered particles,
  transferring the collected fungal particles to a sample chamber,
  dry denaturising the fungal particles,
  detecting voltage changes caused by the denatured fungal particles,
  collecting a sample of the denatured fungal particles,
  wet denaturising the sample,
  analysing the sample in parallel by at least two analysis methods, wherein the analysis methods are selected from immunological detection, glucose measurement and light emission measurement, to obtain measurement data, and
  comparing reference data to obtained measurement data.

The advantages of the present method are essentially identical to those disclosed above in connection with the system and the embodiments listed above in connection with the system apply mutatis mutandis to the method.

According to an embodiment, the filtered particles have a size of 1-40 μm. In certain embodiments, the sizes of the filtered particles may be from 1, 2, 5, 8, 10, 15, 20, 22, 28, 30, 35 or 38 micrometres up to 2, 5, 8, 10, 15, 20, 22, 28, 30, 35, 38 or 40 micrometres.

Embodiments of the present disclosure may enable reliable autonomous determination of quality of air in the building at predefined intervals without requiring any highly skilled experts for performing laboratory experiments of sample liquids.

DETAILED DESCRIPTION OF THE DRAWINGS

Figure 1:
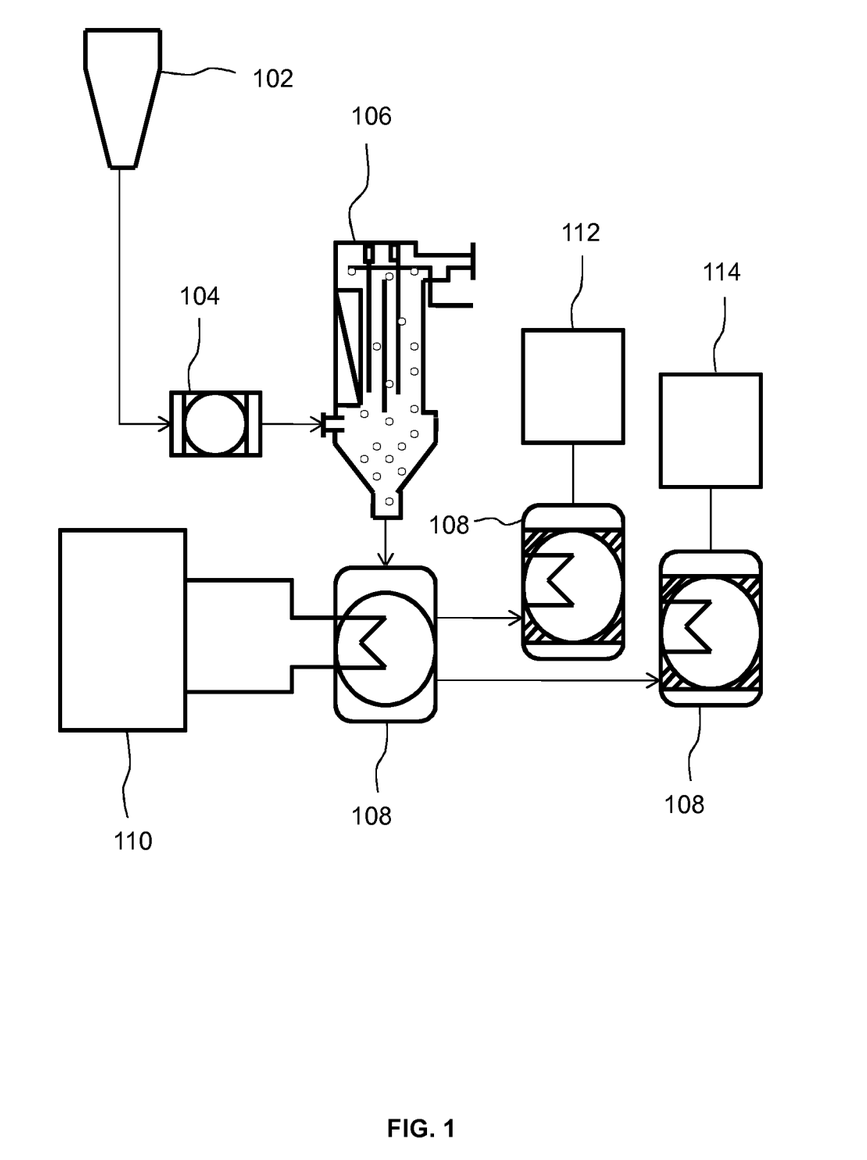
FIG. 1 is a process flow diagram of a system that measures glucose concentration and light emission in a sample liquid in accordance with an embodiment of the present disclosure.

FIG. 1 is a process flow diagram of a system that measures glucose concentration and light emission (in this case fluorescence emission) in sample liquid in accordance with an embodiment of the present disclosure. The system comprises an air inlet 102, a filter 104, a means for collecting fungal particles 106, one sample cuvette 108, a means for heating 110, a means for measuring glucose concentration 112 and a means for measuring fluorescence emission 114. The functions of these parts as have been described above.

Figure 2:
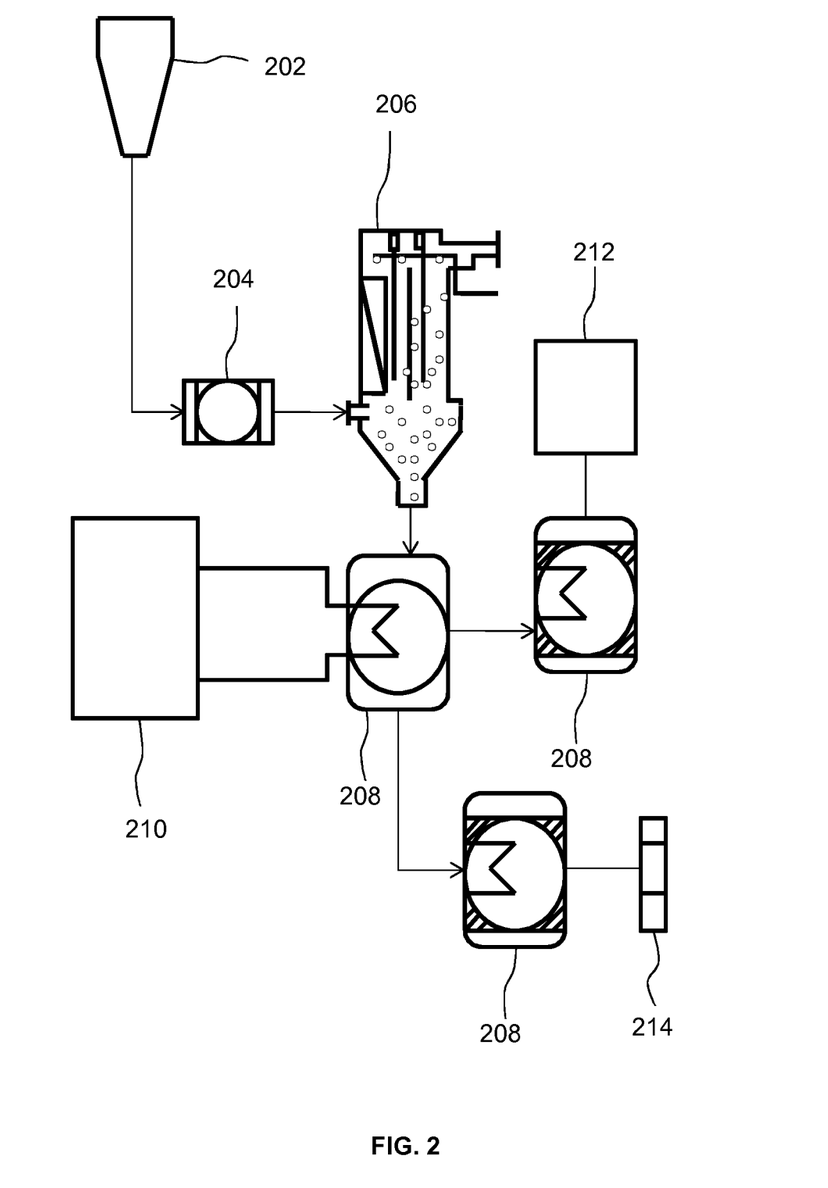
FIG. 2 is a process flow diagram of a system that measures glucose concentration and detects immunological function of fungal species in a sample liquid in accordance with an embodiment of the present disclosure.

FIG. 2 is a process flow diagram of a system that measures glucose concentration and detects immunological function of fungal species in sample liquid in accordance with an embodiment of the present disclosure. The system comprises an air inlet 202, a filter 204, a means for collecting fungal particles 206, one sample cuvette 208, a means for heating 210, a means for measuring glucose concentration 212 and a means for immunological detection of fungal species 214. The functions of these parts as have been described above.

Figure 3:
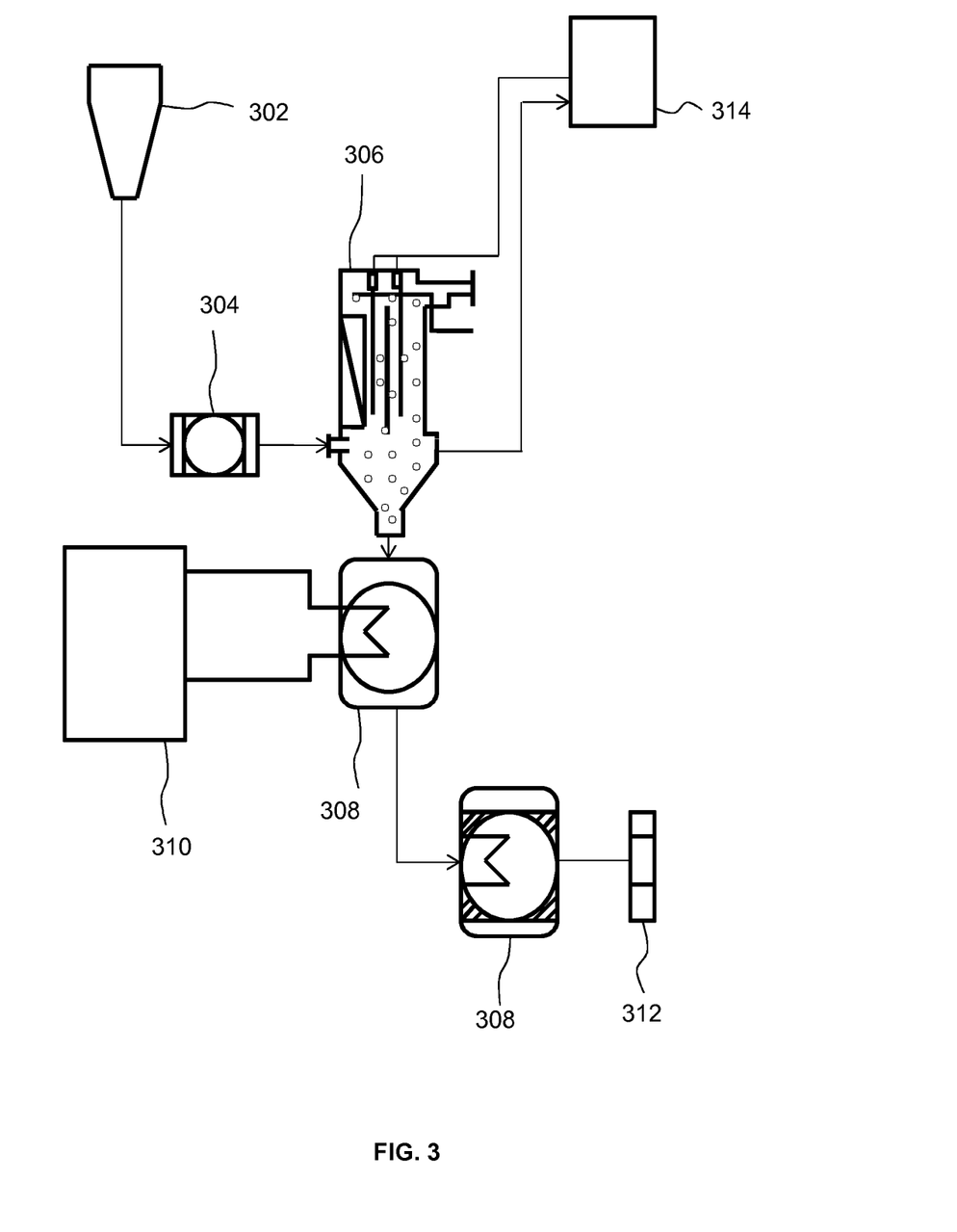
FIG. 3 is a process flow diagram of a system that detects voltage changes and immunological function of fungal species in a sample liquid in accordance with an embodiment of the present disclosure.

FIG. 3 is a process flow diagram of a system that detects voltage changes and immunological function of fungal species in sample liquid in accordance with an embodiment of the present disclosure. The system comprises an air inlet 302, a filter 304, a means for collecting fungal particles 306, one sample cuvette 308, a means for heating 310, a means for immunological detection of fungal species 312 and a means for detection of voltage changes 314. The functions of these parts as have been described above.

Figure 4:
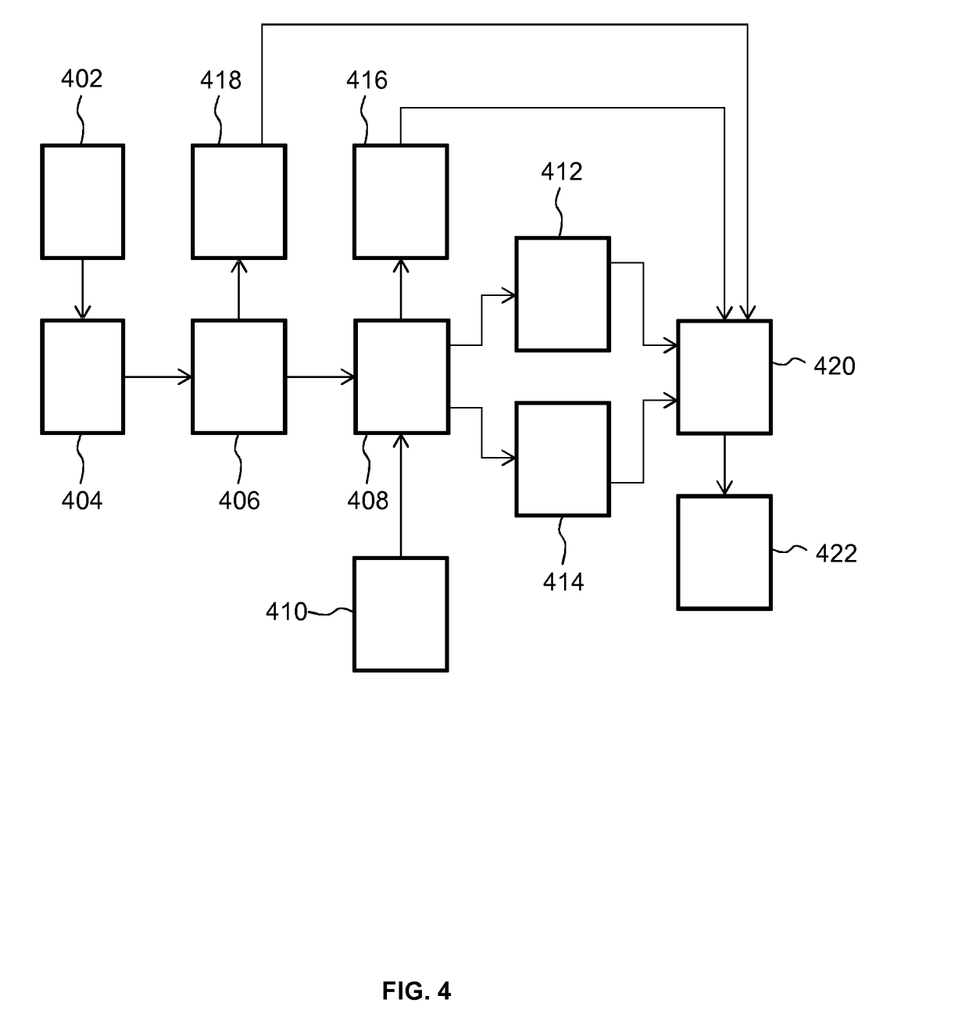
FIG. 4 is a schematic illustration of a system in accordance with an embodiment of the present disclosure.

FIG. 4 is a schematic illustration of a system in accordance with an embodiment of the present disclosure. The system comprises an air inlet 402, a filter 404, a means for collecting fungal particles 406, one sample cuvette 408 and a means for heating 410. The system further comprises at least two of a means for measuring glucose concentration 412, a means for measuring fluorescence emission 414, a means for immunological detection of fungal species 416 and a means for detection of voltage changes 418. The system further comprises a means for collecting and transmitting obtained data 420 and a processor 422. The functions of these parts as have been described above.

Figure 5:
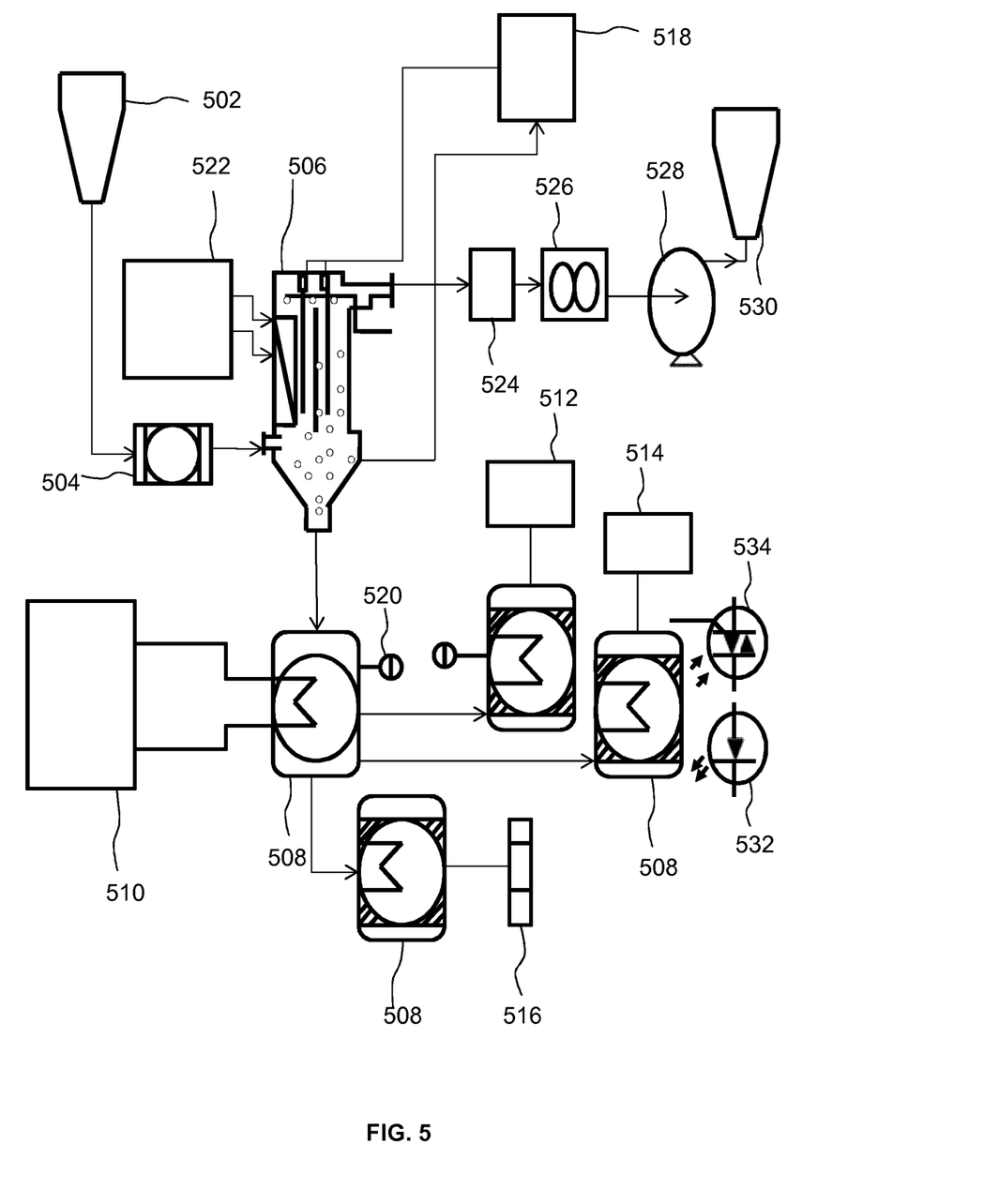
FIG. 5 is a process flow diagram of a system in accordance with an embodiment of the present disclosure.

FIG. 5 is a process flow diagram of a system in accordance with an embodiment of the present disclosure. The system comprises an air inlet 502, a filter 504, a means for collecting fungal particles 506, one sample cuvette 508, a means for heating 510, a means for measuring glucose concentration 512, a means for measuring fluorescence emission 514, a means for immunological detection of fungal species 516 and a means for detection of voltage changes 518. The system further comprises a level sensor 520, a filter heat control 522, an air filter 524, an air flow meter 526, a centrifugal pump 528, an air outlet 530, an emitter 532 and a luminance detector 534. The functions of these parts as have been described above.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A system for determining an amount of fungal particles in air in a building, comprising:
  an air inlet connected to a filter for filtering particles having a size of 1-120 μm,
  means for collecting fungal particles from the filtered particles and transferring the collected fungal particles to at least one sample chamber,
  means for dry denaturation of the fungal particles,
  means for producing a voltage change of the dry denaturised fungal particles and means for detection of voltage changes caused by the dry denaturised fungal particles to obtain voltage change data, means for collecting a sample of the dry denaturised fungal particles,
means for wet denaturation of the sample,
wherein the system further comprises at least two of
  means for immunological detection of the fungal species in the sample to obtain immunological data,
  means for measuring glucose concentration of the sample to obtain glucose concentration data,
  means for measuring light emission of the sample to obtain light emission data,
and the system comprises means for collecting and transmitting the obtained data to a processor, the processor comprising a database of reference data and being configured to compare the reference data to the obtained data for determining the amount of fungal particles in air in the building.

2. A system according to claim 1, wherein the means for collecting fungal particles from the filtered particles is selected from a filter, a condensation plate and a bubbler liquid filter.

3. A system according to claim 1, wherein the means for immunological detection is a group of at least two species specific antigen based immunological test strips.

4. A system according to claim 1, wherein the means for measuring glucose concentration comprises means for treating the sample using temperature and reduced pH and the means is selected from means based on chemical indication, optical polarisation, blue light absorption or magnetic mutual inductance.

5. A system according to claim 1, wherein the means for measuring light emission comprises means for treating the sample using increased pH, solvent and at least one light emission aiding component, excitation means and optical emission measurement means.

6. A system according to claim 1, further comprising means for measuring flow of air at an air outlet of the means for collecting fungal particles.

7. A system according to claim 1, further comprising at least one of a thermometer for obtaining temperature data, means for measuring relative air water content for obtaining relative air water content data and means for measuring absolute air water content for obtaining absolute air water content.

8. A system according to claim 1, further comprising a user interface for displaying the determined amount of fungal particles.

9. A system according to claim 1, further comprising means for raising an alert when the amount of fungal particles in air deviates from target amount of fungal particles in air by a pre-defined amount.

10. A system according to claim 1, wherein the means for detection of voltage changes caused by the fungal particles is based on at least one of electrochemical detection and electrophysical detection.

11. A method for determining an amount of fungal particles in air in a building, comprising:
  periodically injecting a sample of air to a filter for filtering particles having a size of 1-120 μm,
  collecting fungal particles from the filtered particles,
  transferring the collected fungal particles to a sample chamber,
  dry denaturising the fungal particles,
  detecting voltage changes caused by the denatured fungal particles,
  collecting a sample of the denatured fungal particles,
  wet denaturising the sample,
  analysing the sample in parallel by at least two analysis methods, wherein the analysis methods are selected from immunological detection, glucose measurement and light emission measurement, to obtain measurement data, and
  comparing reference data to obtained measurement data.

12. A method according to claim 11, wherein the filtered particles have a size of 1-40 μm.

* * * * *